US006485753B2

(12) United States Patent
Hirowatari et al.

(10) Patent No.: US 6,485,753 B2
(45) Date of Patent: Nov. 26, 2002

(54) DIAGNOSTIC MARKER FOR VASCULAR ENDOTHELIAL INJURY

(75) Inventors: Yuji Hirowatari, Kanagawa-pref. (JP); Hakuo Takahashi, Shiga-pref. (JP); Katsuko Hara, Nara-pref. (JP)

(73) Assignee: Tosoh Corporation, Yamagushi-ken (JP)

( * ) Notice: Subject to any disclaimer, the term of this patent is extended or adjusted under 35 U.S.C. 154(b) by 0 days.

(21) Appl. No.: 09/929,492

(22) Filed: Aug. 15, 2001

(65) Prior Publication Data

US 2002/0052017 A1 May 2, 2002

(30) Foreign Application Priority Data

Aug. 18, 2000 (JP) ........................................ 2000-254236

(51) Int. Cl.$^7$ ............................. A61K 35/16; C12Q 1/00
(52) U.S. Cl. ............................. 424/530; 435/4; 435/372
(58) Field of Search ..................... 435/4, 372; 424/529, 424/530, 531, 532

(56) References Cited

FOREIGN PATENT DOCUMENTS

SU          1642393    *   4/1991

OTHER PUBLICATIONS

Ernberg et al (2000) J. Orofacial Pain 14:37–46.*

* cited by examiner

*Primary Examiner*—David Guzo
*Assistant Examiner*—Bronwen M. Loeb
(74) *Attorney, Agent, or Firm*—Sughrue Mion, PLLC (57) ABSTRACT

A method for diagnosing vascular endothelial injury, which comprises measuring the serotonin level in a plasma sample.

12 Claims, 8 Drawing Sheets

COMPARISON OF PLASMA SEROTONIN LEVELS ACCORDING TO THE PRESENCE OR ABSENCE OF STENOSIS

*Fig.15*

COMPARISON OF PLASMA/BLOOD SEROTONIN LEVELS ACCORDING TO THE PRESENCE OR ABSENCE OF STENOSIS

*Fig.16*

DIAGNOSTIC MARKER FOR VASCULAR ENDOTHELIAL INJURY

FIELD OF THE INVENTION

The present invention relates to a method for diagnosing vascular endothelial injury or arteriosclerotic pathology, i.e., to a method for measuring serotonin which exactly reflects the state of endothelial injury or arteriosclerosis.

DISCUSSION OF BACKGROUND

Coronary artery disease has killed so many people that it is important to detect and treat it in early stages. Coronary artery disease almost always involves arteriosclerotic vascular lesions, and markers for diagnosis of arteriosclerotic pathology and its changes have been sought after. Markers which make it possible to diagnose arteriosclerosis are vital to diagnosis of arteriosclerotic diseases.

Hypercholesterolemia is a risk factor for arteriosclerosis, and cholesterol is considered as an etiogenic agent in the development of arteriosclerotic lesions. The research group organized in 1983 for studies on primary hyperlipidemia by the Ministry of Health and Welfare under a research project against specific diseases reported that the prevalence of coronary artery disease increases about five times from 2.3% to 12.9% with increase in serum cholesterol from 199 mg/dl or below to 400 mg/dl or above. In recent years, LDL cholesterol, oxidized LDL and other etiogenic agents for arteriosclerosis have been studied as diagnostic markers for diagnosis of arteriosclerotic pathology.

Another risk factor for arteriosclerotic disease under study is an inflammation marker, CRP (C-reactive protein) (Paul M. Ridker et al., The New England J. Medicine, 23, p.836, 2000) because inflammation of the arteriosclerotically injured vascular endothelium is accompanied by increase of CRP, which serves as an inflammation marker. However, because the CRP level (concentration) increases not only after vascular endothelial injury the but also after destruction of organ tissues and bacterial infection, CRP has a problem with specificity and is improper for exact diagnosis of arteriosclerotic pathology and vascular endothelial injury.

SUMMARY OF THE INVENTION

As discussed above, diagnostic markers for endothelial injury are essential important not only for diagnosis of vascular endothelial injury but also for diagnosis of arteriosclerotic pathology. The object of the present invention is to provide a substance which serves as a novel diagnostic marker for endothelial injury and arteriosclerotic pathology.

A search for a novel marker to attain the above-mentioned object hit on serotonin, the level of which in plasma increases upon development of a gastrointestinal tumor (Ming-shih Lee, et al., Clinical Chemistry, 46, p.422 (2000)) or a carcinoid tumor from secretory cells in the gastrointestinal tract (Kiyoshi Saijo, Nihon Rinsho, 53, p.527 (1995)). It is known that plasma serotonin transiently increases at the sites of stenosis in the coronary artery during coronary angioplasty (Paolo Golino et al, The New England J. Medicine, 330, P.523 (1994), and Dario Leosco et al., The American J. Cardiology, 84, p.1317 (1999)). However, it is also reported that there was no change in the plasma serotonin level in abdominal aortic blood during coronary angioplasty (Paolo Golino et al., The New England J. Medicine, 330, p.523 (1994)).

The results of measurements of serotonin in platelet-rich plasma obtained by centrifuging blood from patients with coronary artery disease for 5 minutes at 450×g revealed that the serotonin level is significantly higher in patients younger than 60 years old than in normal subjects without coronary artery disease (Kjell Vikenes et al., Circulation, 100, p.483, 1999). However, there has been no report that suggests ectoglobular free serotonin outside of the platelets in blood, or serotonin in platelet-free plasma, as a marker for diagnosis of vascular endothelial injury and arteriosclerotic pathology.

The plasma serotonin levels in carcinoid patients are higher than those in healthy people. Comparison between a group of carcinoid patients with coronary heart disease and a noncardiac group of carcinoid patients demonstrated that the plasma serotonin level in the cardiac group was significantly higher (Paul A. et al., Circulation, 92, p.790–795 (1995)). However, the results were obtained with a particular group of patients having carcinoids with high plasma serotonin levels and do not suggest association of plasma serotonin with vascular endothelial injury or arteiosclerotic disease in non-carcinoid individuals.

Therefore, in order to attain the above-mentioned object, according to the first aspect of the present invention, the present invention provides a method for diagnosing vascular endothelial injury, which comprises measuring the serotonin level in a plasma sample. In order to attain the above-mentioned object, according to the second aspect of the present invention, the present invention provides a method for diagnosing vascular endothelial injury, which comprises measuring the ratio of the serotonin level in a plasma sample to the serotonin level in a blood sample, a serum sample or a platelet sample. In order to attain the above-mentioned object, according to the third aspect of the present invention, the present invention provides a method for diagnosing arteriosclerotic pathology, which comprises measuring the serotonin level in a plasma sample. In order to attain the above-mentioned object, according to the fourth aspect of the present invention, the present invention provides a method for diagnosing arteriosclerotic pathology, which comprises measuring the ratio of the serotonin level in a plasma sample to the serotonin level in a blood sample, a serum sample or a platelet sample. Now, the present invention is described in detail.

DETAILED DESCRIPTION OF THE PREFERRED EMBODIMENTS

The high prevalence of coronary artery disease tendency among elderly people over the age of 40 or 50 suggests that many of the people over the age of 40 or 50 in a group of allegedly normal individuals have arteriosclerotic lesions developed from vascular endothelial injury at high risk of coronary artery disease. From this point of view, the plasma serotonin levels and the ratios of plasma/blood or platelet serotonin in normal people between the ages of 20 to 70 were determined and compared by age. Further, the plasma serotonin levels and the ratios of plasma/blood or platelet serotonin in patients with arterioscelotic lesions were determined before detection of the arterioscelotic lesions by coronary angiography (CAG) and subsequent coronary angioplasty (PCTA).

The ratio of plasma/blood or platelet serotonin was significantly higher in the age bracket of 40 or more among the normal people. The comparison between the patients who were specified as having arterioscelotic lesions by CAG and underwent PTCA and the normal people at ages of 40 or above revealed that plasma serotonin and the plasma/blood or platelet serotonin were significantly higher in the group of patients who underwent PTCA.

These results suggests that by measuring plasma serotonin level and the ratio of plasma/blood or platelet serotonin, it is possible to detect and predict endothelial injury and arteriosclerosis. The above-mentioned variables of serotonin can be diagnostic markers to monitor arteriosclerotic pathology, and that these variables can be indicators of the risk of coronary artery disease. It is possible to equate the serum serotonin level with the blood serotonin level because platelets release serotonin during blood coagulation (Saijo Kiyoshi, Nihon Rinsho, 53, p.527, (1995 Supplement)). It is also possible to equate the serotonin level in platelet-rich plasma obtained from whole blood after 5 minutes of centrifugation at 450×g with the blood serotonin level because most of the blood serotonin exists in platelets.

Serotonin is produced by enterochromaffin cells in the gastrointestinal mucosa and released into blood. Platelets do not produce serotonin by themselves and take up serotonin from blood and store it. Because production of serotonin by enterochromaffin cells can vary from person to person, the ratio of the plasma serotonin level to the blood (whole blood or serum) serotonin level or the platelet serotonin level is more reliable and preferable as a diagnostic marker than the plasma serotonin level.

It is supposed that the platelet serotonin level drops in the presence of an arteriosclerotic lesion because activation of platelets by the arteriosclerotic lesion sets off release of serotonin from the activated platelets which results in increase of the plasma serotonin level, and the released serotonin further activates platelets by stimulating serotonin receptors (5HT2 receptor) on platelets. It means that the ratio of the plasma serotonin level to the blood (blood or serum) serotonin level or the platelet serotonin level reflects pathological change more numerically than the plasma serotonin level.

In measurement of plasma serotonin, it is crucial to prevent release of serotonin from platelets into blood. Because activation of platelets (coagulation) sets off release of serotonin from platelets, it is preferred to keep calcium ions, which play a major role in activation of platelets, trapped during measurement of serotonin and preparation of plasma samples from blood. For example, measurement may be carried out in the presence of an anticoagulant which hinders blood coagulation by capturing calcium ions. Anticoagulants which not only are easy to handle and obtain and have strong anticoagulant effect but also leave collected blood samples available for measurement of other blood components are preferable. As a specific example of such anticoagulants, ethylenediaminetetraacetic acid (hereinafter referred to as EDTA) or citric acid may be mentioned. EDTA is particularly preferred because citric acid is likely to damage platelets by making blood slightly acidic and induce release of serotonin, though in a trace amount, from the damaged platelets.

EDTA in the form which does not change the pH of blood when mixed with the blood is particularly preferred, because platelets can be damaged from change in pH and release serotonin. A particularly preferable forms of EDTA is dipotassium EDTA dihydrate (EDTA-2K) or disodium EDTA (EDTA-2Na). Dipotassium EDTA dihydrate is particularly preferable by virtue of its fast dissolution. Slow dissolution would lead to local increase in the salt concentration which causes damage to platelets. EDTA is usually added to blood as an anticoagulant at concentrations from 0.025 to 0.049 mol/l in blood. However, it was found that measurement of serotonin in the presence of EDTA in this concentration range gives high values for some samples. This finding suggests that EDTA in this concentration range can not completely prevent activation of platelets and allows gradual release of serotonin from platelets. On the other hand, osmotic damage from high EDTA concentrations can induce platelets to release serotonin. Therefore, the EDTA concentration in blood for use in measurement of serotonin or preparation of plasma samples is, for example, from 0.0074 to 0.0148 mol/l, preferably from 0.008 to 0.014 mol/l. It is particularly preferred to carry out the whole procedure from preparation of plasma samples from blood to measurement of serotonin in the presence of EDTA in the above-mentioned concentration range.

Specifically, in the present invention, serotonin may, for example, be measured by liquid chromatography (Japanese Unexamined Patent Publication JP-A-13–56326) or by an ordinary immunological method using a serotonin-specific antibody.

EXAMPLE 1

Blood (whole blood) samples were drawn from the intermediate cubital veins of normal subjects (with total blood cholesterol levels of at most 220 mg/dl) between the ages of 20–29 (3 men and 3 women), between the ages of 30–39 (15 men and 4 women), between the ages of 40–49 (5 men and 3 women), between the ages of 50–59 (7 men and 5 women) and between the ages of 70–79 (1 man and 2 women) into blood collection tubes containing EDTA-2K as an anticoagulant (Becton Dickinson; blood collection tubes with a dipotassium ethylenediaminetetraacetate dihydrate concentration of 2 mg/ml) with their consent. Part of each whole blood sample was centrifuged at 1000×g at 4° C. for 25 minutes to separate a plasma sample. The platelet serotonin was calculated by subtracting the plasma serotonin level from the blood serotonin level.

Tables 1 to 5 show the mean serotonin levels in the samples with the standard deviations. Table 6 shows the values of p obtained by the two-tailed Student's t-test on the samples from the 15 men and the 4 women between the ages 30–39, the samples from the 5 men and the 3 women between the ages 40–49, the samples from the 7 men and the 5 women between the ages 50–59 and the samples from the 1 man and the 2 women at ages of 70 or above.

TABLE 1

Plasma serotonin level

|  | Mean (nmol/l) | S.D. (nmol/l) |
|---|---|---|
| Ages of 20–29 | 3.67 | 1.92 |
| Ages of 30–39 | 5.89 | 3.47 |
| Ages of 40–49 | 7.04 | 4.15 |
| Ages of 50–59 | 5.78 | 2.73 |
| Ages of 70– | 6.08 | 3.36 |

TABLE 2

Blood serotonin level

|  | Mean (nmol/l) | S.D. (nmol/l) |
|---|---|---|
| Ages of 20–29 | 68.1 | 27.8 |
| Ages of 30–39 | 106.6 | 38.9 |
| Ages of 40–49 | 66.3 | 24.9 |
| Ages of 50–59 | 64.0 | 29.2 |
| Ages of 70– | 59.6 | 25.0 |

TABLE 3

Platelet serotonin level

|  | Mean (nmol/l) | S.D. (nmol/l) |
|---|---|---|
| Ages of 20–29 | 64.45 | 26.41 |
| Ages of 30–39 | 100.72 | 7.44 |
| Ages of 40–49 | 59.22 | 23.43 |
| Ages of 50–59 | 58.18 | 27.96 |
| Ages of 70– | 53.53 | 21.83 |

TABLE 4

Plasma serotonin/blood serotonin

|  | Mean (%) | S.D. (%) |
|---|---|---|
| Ages of 20–29 | 5.34 | 1.98 |
| Ages of 30–39 | 5.90 | 3.29 |
| Ages of 40–49 | 11.14 | 5.81 |
| Ages of 50–59 | 9.75 | 3.51 |
| Ages of 70– | 9.81 | 1.84 |

TABLE 5

Plasma serotonin/platelet serotonin

|  | Mean (%) | S.D. (%) |
|---|---|---|
| Ages of 20–29 | 5.68 | 2.20 |
| Ages of 30–39 | 6.40 | 3.85 |
| Ages of 40–49 | 12.97 | 7.62 |
| Ages of 50–59 | 10.96 | 4.31 |
| Ages of 70– | 10.91 | 2.29 |

TABLE 6

Values of p obtained by the two-tailed Student's t-test when compared with the group between the ages of 30–39

|  | Ages of 40–49 | Ages of 50–59 | Ages of 70– |
|---|---|---|---|
| Plasma serotonin | 0.4653 | 0.925 | 0.9335 |
| Blood serotonin | 0.0123 | 0.0029 | 0.0584 |
| Platelet serotonin | 0.0079 | 0.0021 | 0.0487 |
| Plasma/blood serotonin | 0.0062 | 0.0043 | 0.0615 |
| Plasma/platelet serotonin | 0.0059 | 0.0046 | 0.0649 |

Both the ratio of plasma/blood serotonin and the ratio of plasma/platelet serotonin were significantly higher at the ages of 40 or above. Considering the high prevalence of arteriosclerotic coronary artery disease beyond the age of 40 or 50, the results indicate that the ratios of plasma/blood serotonin and plasma/platelet serotonin serves as diagnostic markers to monitor arteriosclerotic pathology and as diagnostic markers for vascular endothelial injury.

In the present example, the measurement was done by the procedure disclosed in Example 1 of Japanese Unexamined Patent Publication JP-A-13–56326 using a commercial column (TSK gel ODS-80Ts (Product name), Tosoh Corporation). The whole blood samples and the plasma samples were diluted 20-fold with a diluent prepared by homogeneously admixing 0.19 g of ascorbic acid, 0.38 g of EDTA 2Na and 34 ml of 60% perchloric acid solution with 1 l of pure water and centrifuged at 10000×g for 5 minutes. The supernatants were used for the measurement.

The lower blood serotonin and platelet serotonin levels at ages of 40–49, 50–59 and 70- as compared with those at ages of 30–39 may be explained in terms of reduced production of serotonin by enterochromaffin cells. FIGS. 1 to 5 show these results as bar graphs. The error bars in the graphs indicate 95% confidence intervals.

EXAMPLE 2

Blood (whole blood) samples were drawn from the intermediate cubital veins of patients with arterioscelotic lesions (18 men and 4 women) into blood collection tubes (Becton Dickinson) containing an anticoagulant, EDTA-2K, before detection of the arterioscelotic lesions by coronary angiography (CAG) and subsequent coronary angioplasty (PTCA), and the samples were assayed in the same manner as in Example 1. The results were compared with the results obtained in Example 1 with respect to the people at the ages of 40 or above because all the patients tested were at least 40 years old.

Table 7 shows the means and the standard deviations, and Table 8 shows the values of p obtained by the two-tailed Student's t-test. FIGS. 6–10 are bar graphs showing the results. The error bars in the graphs indicate 95% confidence intervals.

TABLE 7

Means and standard deviations

|  | Patients | | Non-patients | |
| --- | --- | --- | --- | --- |
|  | Mean | S.D. | Mean | S.D. |
| Plasma serotonin (nmol/l) | 9.55 | 8.15 | 6.26 | 3.25 |
| Blood serotonin (nmol/l) | 70.68 | 41.51 | 64.20 | 26.18 |
| Platelet serotonin (nmol/l) | 61.13 | 41.83 | 57.94 | 24.74 |
| Plasma/blood serotonin (nmol/l) | 20.83 | 25.03 | 10.24 | 4.20 |
| Plasma/platelet serotonin (nmol/l) | 82.75 | 218.51 | 11.65 | 5.40 |

TABLE 8 p values obtained by two-tailed Student's t-test

|  | Value of p |
| --- | --- |
| Plasma serotonin | 0.0796 |
| Blood serotonin | 0.5322 |
| Platelet serotonin | 0.7558 |
| Plasma/blood serotonin | 0.0517 |
| Plasma/platelet serotonin | 0.1259 |

Comparison of the results obtained for the group examined by CAG with the results obtained in Example 1 for the group of people at the ages of 40 or above who were not examined by coronary angiography (CAG) revealed significant difference in plasma serotonin between the two groups (p=0.0796). There was more significant difference in the ratio of plasma/blood serotonin between the two groups (p=0.0517). Considering that the patients who were specified as having arterioscelotic lesions by CAG and received PTCA had arteriosclerotic disease and vascular endothelial injury, these results suggest that the ratio of plasma/blood serotonin is useful as a diagnostic marker for diagnosis of arteriosclerotic pathology or for diagnosis of vascular endothelial injury.

The ratio of plasma/platelet serotonin was obviously higher in the patients who were proven to have arteriosclerotic lesions by CAG and received PTCA than in the people who did not get CAG. This indicates that the ratio of plasma/platelet serotonin can be used as a diagnostic marker for diagnosis of arteriosclerotic pathology or for diagnosis of vascular endothelial injury.

However, analysis of the values for the patient group on an individual basis revealed a large standard deviation due to the presence of some patients with low plasma/platelet serotonin ratios, and the difference in the ratio of plasma/platelet serotonin is less significant than that in plasma serotonin and that in the ratio of plasma/blood serotonin.

EXAMPLE 3

Blood was drawn from three patients with their consent, and the blood from each patient was dispensed into 8 tubes containing 2, 4, 6, 8, 10, 12, 14 and 16 mg of dipotassium EDTA dihydrate (EDTA-2K), 2 ml each, and gently shaken. The EDTA-2K concentrations of the resulting blood mixtures were 0.025, 0.049, 0.0074, 0.0099, 0.0124, 0.0148, 0.0173 and 0.0198 mol/l, respectively.

A 50 µl portion from each blood mixture was mixed with 1 ml of a solution containing 8 ml of 60% perchloric acid and 7.04 g of ascorbic acid in 192 ml of pure water and centrifuged at 4° C., 10000×g for 5 minutes. The supernatants were mixed with the equivalent volumes of a solution containing 4.9 g of sodium perchlorate and 0.07 g of EDTA-2Na in 198 ml of pure water and assayed in the same manners as in Example 1 as whole blood samples.

On the other hand, the remaining blood mixtures were centrifuged at 4° C., 1000×g for 25 minutes to separate platelet poor plasma. A 250 µl portion of each platelet poor plasma sample was mixed with 1 ml of a solution containing 13.4 ml of 60% perchloric acid and 0.44 g of ascorbic acid in 187 ml of pure water and centrifuged at 4° C., 1000×g for 5 minutes. The supernatants were mixed with the equivalent volumes of a solution containing 4.9 g of sodium perchlorate and 0.07 g of EDTA-2Na in 198 ml of pure water and assayed in the same manners as in Example 1 as plasma samples.

Table 9 show some of the results of the whole blood serotonin assay, and almost the same measurements were obtained despite the difference in the concentration of EDTA-2K added. Table 10 show the results of the measurement of the plasma serotonin levels. Concerning plasma samples from patient 1, the measurements were not higher than 10 nmol/l at EDTA-2K concentrations of 0.0074 to 0.0148 mol/l, while as high measurements as at least 10 nmol/l were obtained at EDTA-2K concentrations of at most 0.0049 mol/l, or at least 0.0173 mol/l. With respect to plasma samples from patient 2, about the same measurements were obtained at all the EDTA-2K concentrations. With respect to patient 3, the plasma sample containing 0.0198 mol/l of EDTA-2K gave a higher measurement than the other samples. The high measurement of plasma serotonin obtained with the plasma samples from patient 1 at EDTA concentration of 0.0173 mol/l or above and obtained with the plasma sample from patient 3 at the EDTA concentration of 0.0198 mol/l suggest release of platelet serotonin induced by the osmotic damage to platelets from the high EDTA concentrations.

TABLE 9

Relation between the EDTA concentration in blood collection tubes and the blood serotonin level

| EDTA concentration (nmol/l) | Blood serotonin level (nmol/l) | |
|---|---|---|
| | Patient 1 | Patient 2 |
| 0.0025 | 554.23 | 392.64 |
| 0.0049 | 584.27 | 404.70 |
| 0.0074 | 563.44 | 407.61 |
| 0.0099 | 571.47 | 416.86 |
| 0.0124 | 519.30 | 424.76 |
| 0.0148 | 575.38 | 420.22 |
| 0.0173 | 596.06 | 394.46 |
| 0.0198 | 577.02 | 432.77 |

TABLE 10

Relation between the EDTA concentration in blood collection tubes and the plasma serotonin level

| EDTA concentration (nmol/l) | Plasma serotonin level (nmol/l) | | |
|---|---|---|---|
| | Patient 1 | Patient 2 | Patient 3 |
| 0.0025 | 16.23 | 4.77 | 13.32 |
| 0.0049 | 15.75 | 3.81 | 10.50 |
| 0.0074 | 6.69 | 3.68 | 14.19 |
| 0.0099 | 5.87 | 5.61 | 10.45 |
| 0.0124 | 9.25 | 3.04 | 11.90 |
| 0.0148 | 7.01 | 5.41 | 12.63 |
| 0.0173 | 11.25 | 4.95 | 12.58 |
| 0.0198 | 10.58 | 4.51 | 84.72 |

EXAMPLE 4

Blood was drawn from 21 normal subjects (with total blood cholesterol levels of at most 190 mg/l) (n=9 between the ages 20–29 and n=12 between the ages between 40–49) and 65 patients with coronary artery disease (between the ages 30–79) with their consent, and the blood and plasma serotonin levels were measured. 2 ml of blood was collected in each blood collection tube with a 2 ml volume containing 6 mg of EDTA-2K.

A 50 μl portion of each blood mixture was mixed with 1 ml of a solution containing 8 ml of 60% perchloric acid and 7.04 g of ascorbic acid in 192 ml of pure water and centrifuged at 4° C., 1000×g for 5 minutes. The supernatants were mixed with the equivalent volumes of a solution containing 4.9 g of sodium perchlorate and 0.07 g of EDTA-2Na in 198 ml of pure water and assayed in the same manners as in Example 1 as whole blood samples.

On the other hand, the remnants of the blood mixtures were centrifuged at 4° C., 1000×g for 25 minutes to separate platelet poor plasma. A 250 μl portion of each platelet poor plasma sample was mixed with 1 ml of a solution containing 13.4 ml of 60% perchloric acid and 0.44 g of ascorbic acid in 187 ml of pure water and centrifuged at 4° C., 10000×g for 5 minutes. The supernatants were mixed with the equivalent volumes of a solution containing 4.9 g of sodium perchlorate and 0.07 g of EDTA-2Na in 198 ml of pure water and assayed in the same manners as in Example 1 as plasma samples.

Table 11 shows the blood and plasma serotonin levels and the ratios of plasma/blood serotonin in the healthy people between the ages of 20–29 and between the ages of 40–49. There was no significant difference by age, although significant differences by age were recognized in Example 1. The lack of significant difference in the plasma serotonin level and the ratio of plasma/blood serotonin by age is attributable to the definition of normal people as having total cholesterol levels of at most 190 mg/dl. The fact that the plasma serotonin level and the ratio of plasma/blood serotonin were significantly higher in older people in Example 1 in which normal people were defined as having total cholesterol levels of at most 220 mg/dl, suggests the presence of arteriosclerotic patients in the normal group in Example 1. Because there was no differences by age among the normal subjects who supplied samples in the present Example as described above, age was not taken into consideration in the subsequent comparison with the patient group.

Though the collected blood was treated by different methods at different EDTA concentrations in the present Example and Example 1, the treatment method employed in the present Example enables more accurate and precise measurement of plasma and blood serotonin and gives lower plasma serotonin levels, higher blood serotonin levels and smaller ratios of plasma/blood serotonin than that employed in Examples 1 and 2.

Figure 1:
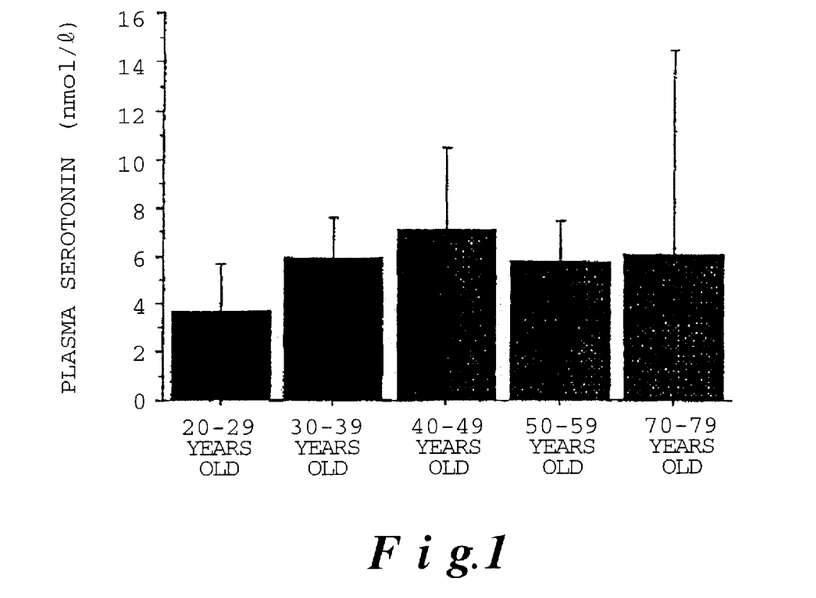
FIG. 1 is a histogram showing the plasma serotonin levels determined in Example 1. The error bars in the graph indicate 95% confidence intervals.
Figure 2:
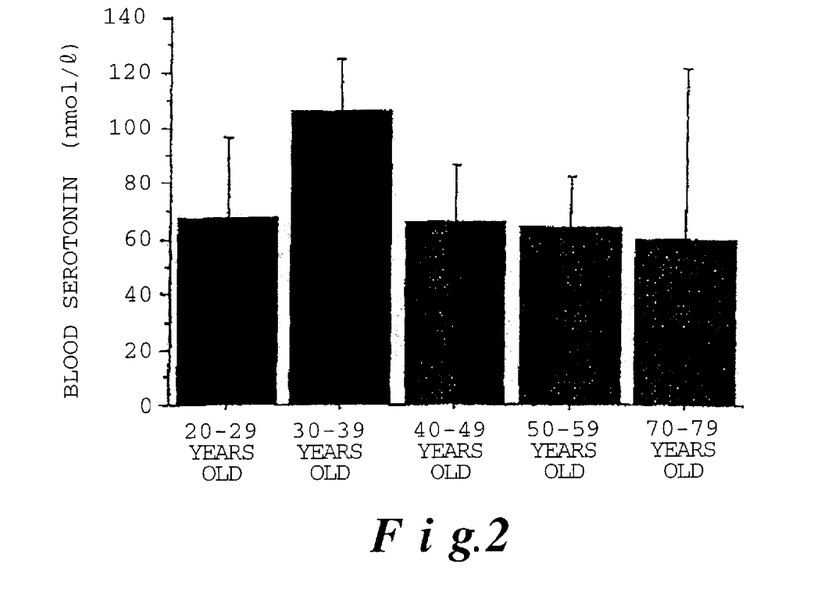
FIG. 2 is a histogram showing the blood serotonin levels determined in Example 1. The error bars in the graph indicate 95% confidence intervals.
Figure 3:
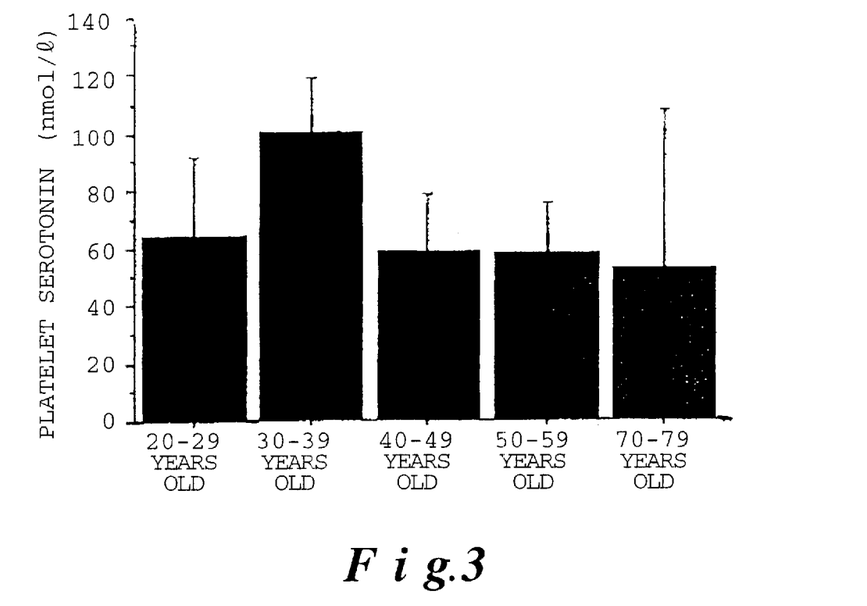
FIG. 3 is a histogram showing the platelet serotonin levels determined in Example 1. The error bars in the graph indicate 95% confidence intervals.
Figure 4:
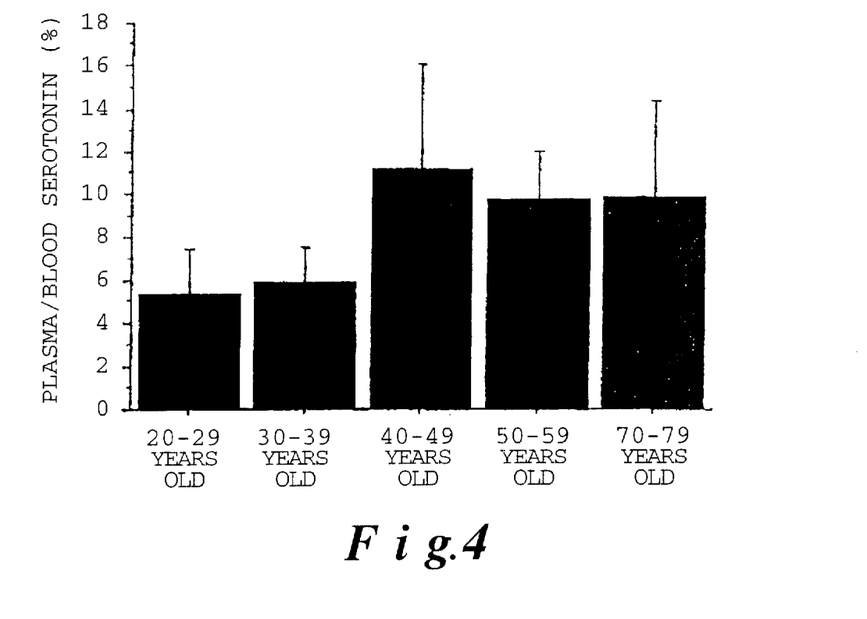
FIG. 4 is a histogram showing the ratios of plasma/blood serotonin determined in Example 1. The error bars in the graph indicate 95% confidence intervals.
Figure 5:
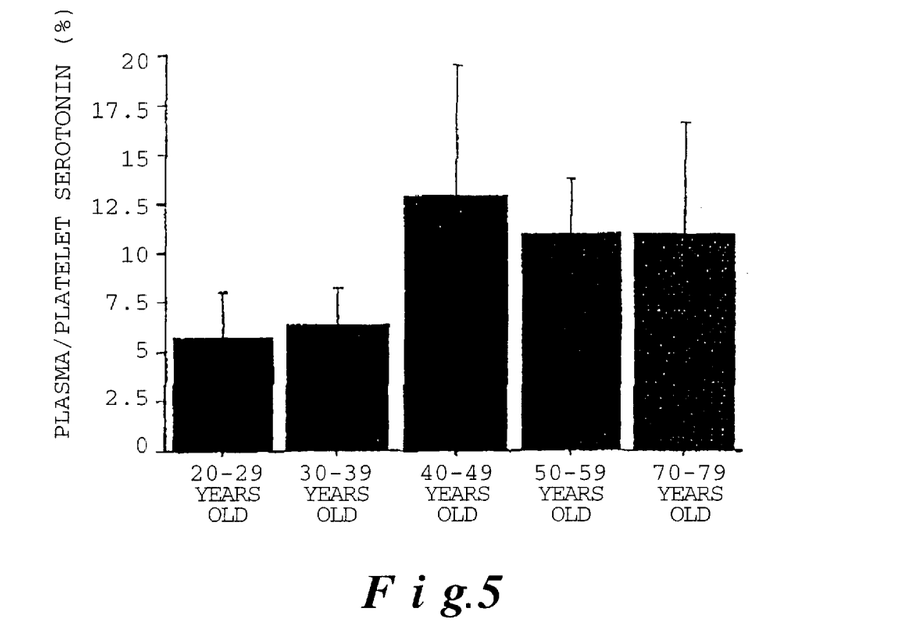
FIG. 5 is a histogram showing the ratios of plasma/platelet serotonin determined in Example 1. The error bars in the graph indicate 95% confidence intervals.
Figure 6:
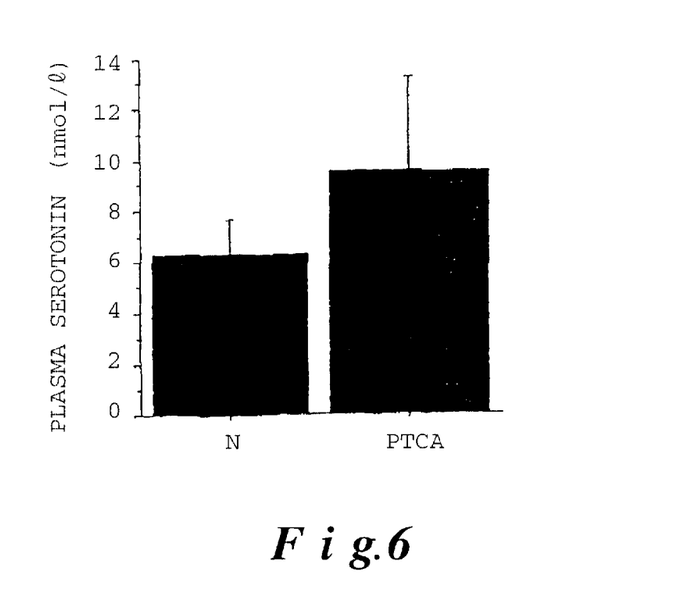
FIG. 6 is a histogram showing the plasma serotonin levels determined in Example 2. The error bars in the graph indicate 95% confidence intervals. N denotes the non-examined group, and PTCA denotes the group of patients who were proved to have arterioscelotic lesions by coronary angiography (CAG) and received percutaneous transluminal coronary angioplasty (PTCA).
Figure 7:
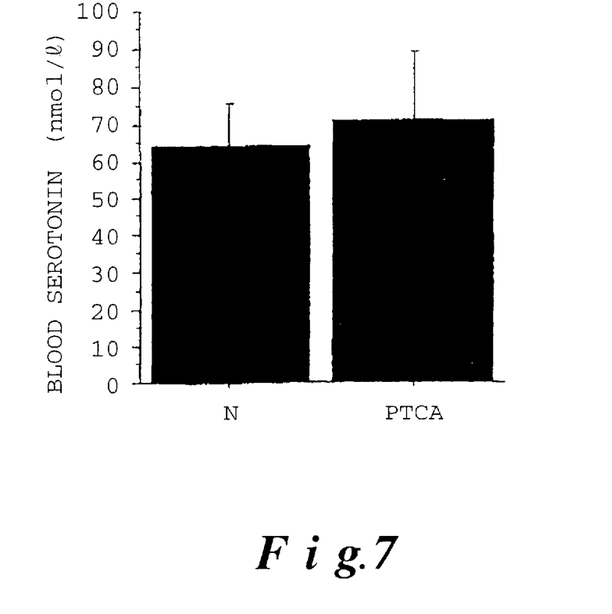
FIG. 7 is a histogram showing the blood serotonin levels determined in Example 2. The error bars in the graph indicate 95% confidence intervals. N denotes the non-examined group, and PTCA denotes the group of patients who were proved to have arterioscelotic lesions by coronary angiography (CAG) and received percutaneous transluminal coronary angioplasty (PTCA).
Figure 8:
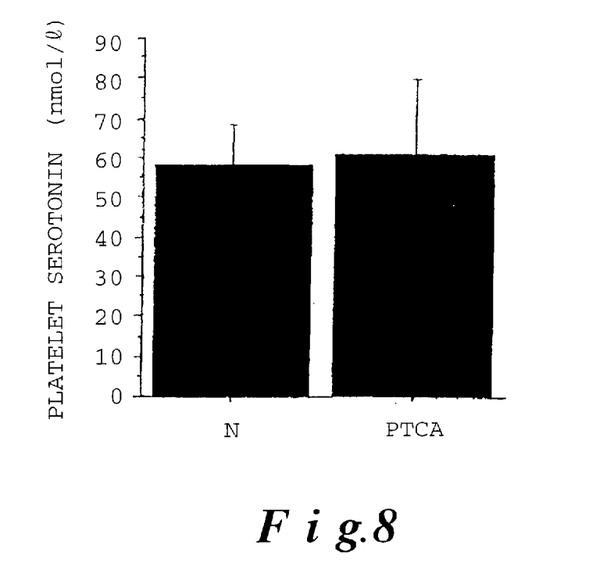
FIG. 8 is a histogram showing the blood serotonin levels determined in Example 2. The error bars in the graph indicate 95% confidence intervals. N denotes the non-examined group, and PTCA denotes the group of patients who were proved to have arterioscelotic lesions by coronary angiography (CAG) and received percutaneous transluminal coronary angioplasty (PTCA).
Figure 9:
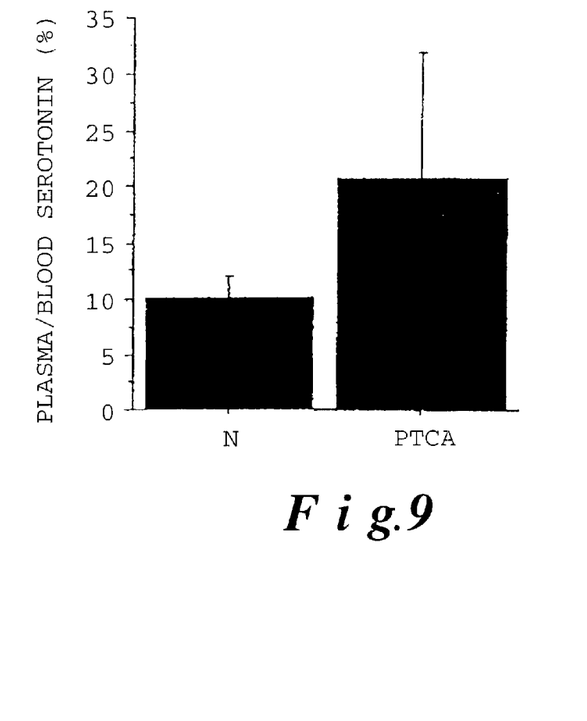
FIG. 9 is a histogram showing the ratios of plasma/blood serotonin determined in Example 2. The error bars in the graph indicate 95% confidence intervals. N denotes the non-examined group, and PTCA denotes the group of patients who were proved to have arterioscelotic lesions by coronary angiography (CAG) and received percutaneous transluminal coronary angioplasty (PTCA).
Figure 10:
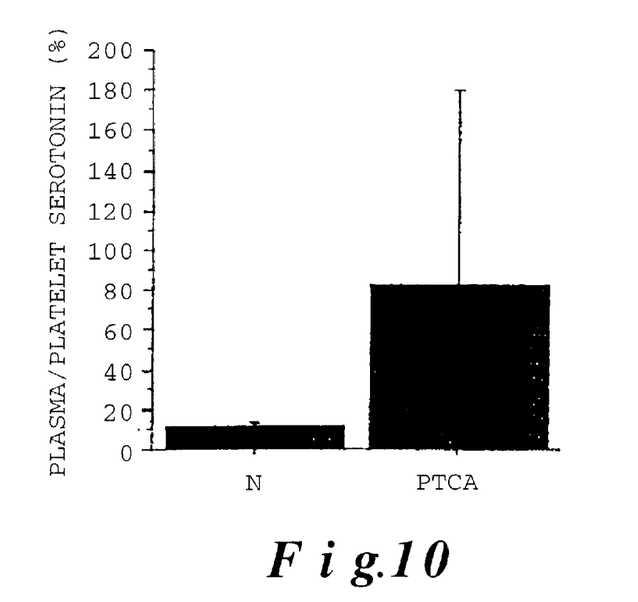
FIG. 10 is a histogram showing the ratios of plasma/platelet serotonin determined in Example 2. The error bars in the graph indicate 95% confidence intervals. N denotes the non-examined group, and PTCA denotes the group of patients who were proved to have arterioscelotic lesions by coronary angiography (CAG) and received percutaneous transluminal coronary angioplasty (PTCA).
Figure 11:
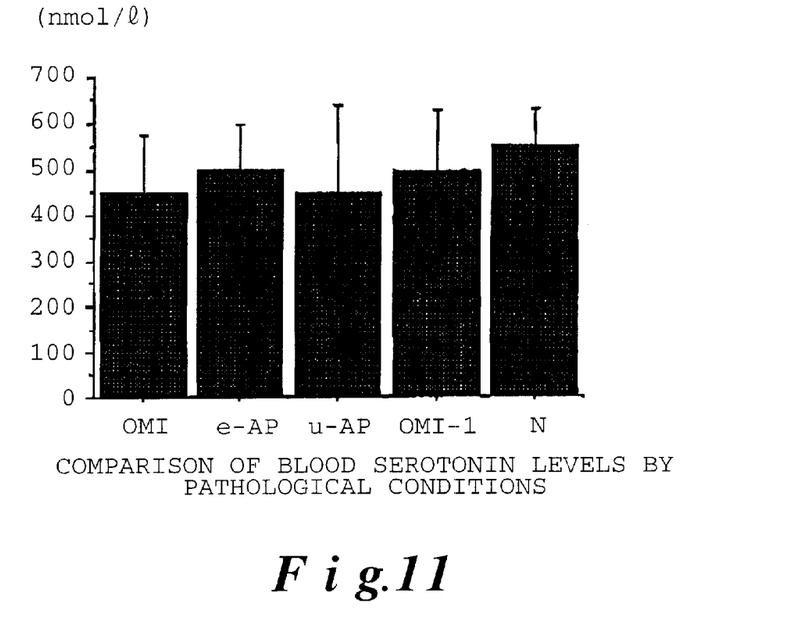
FIG. 11 is a histogram showing the blood serotonin levels determined in Example 4. The error bars in the graph indicate 95% confidence intervals.
Figure 12:
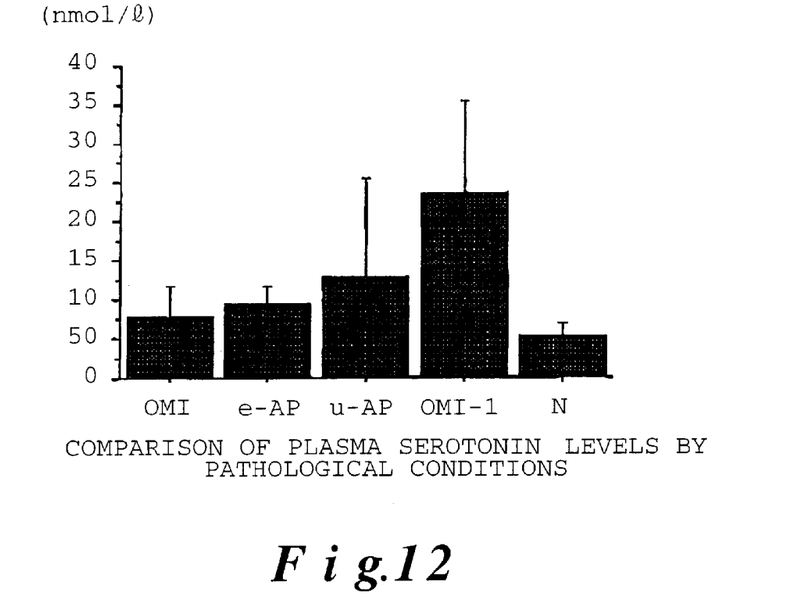
FIG. 12 is a histogram showing the plasma serotonin levels determined in Example 4. The error bars in the graph indicate 95% confidence intervals.
Figure 13:
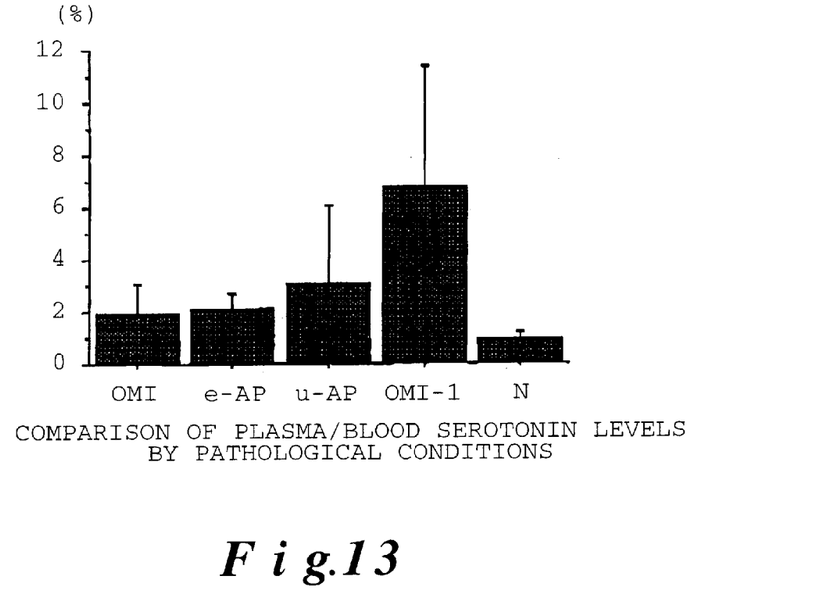
FIG. 13 is a histogram showing the plasma/blood serotonin determined in Example 4. The error bars in the graph indicate 95% confidence intervals.

Tables 12 to 14 and FIGS. 11 to 13 show the results obtained with blood from the 65 patients with coronary artery disease subgrouped pathologically as those who had experienced the onset of old myocardial infarction more than a year before (n=18, 30–79 years old, hereinafter referred to as MOI), those with exertional angina (n=24, 50–79 years old, hereinafter referred to as e-AP), those with unstable angina (n=5, 40–79 years old, hereinafter referred to as u-AP) and those who had experienced the onset of old myocardial infarction within a year (n=18, 50–79 year old, hereinafter referred to as OMI-1), and the normal subjects (hereinafter referred to as N).

The N group was the lowest in the plasma serotonin level and the ratio of plasma/blood serotonin, and the OMI, e-AP, u-AP and OMI-1 groups followed in this order. These results indicate that the u-AP group suffered severer vascular endothelial injury, at least in a pathological sense, than the e-AP group, and that the vascular endothelial injury in the OMI group, as long as they were under proper treatment, was in better conditions than that in the OMI-1 group. Actually, with respect to the plasma serotonin level and the ratio of plasma/blood serotonin, the u-AP group was higher than the e-AP group, and the OMI-1 group was higher than the OMI group.

Analyses of the results by the p-test (in which values of $p<0.05$ were considered significant) revealed significant differences in the plasma serotonin level between the e-AP, u-AP and OMI-1 groups versus the N group, between the OMI-1 versus the OMI group and between the OMI-1 group versus the e-AP group and significant differences in the ratio of plasma/blood serotonin between the OMI, e-AP, u-AP and OMI-1 groups versus the N group, between the OMI-1 group versus e-AP group. The significance of the differences between the e-AP and u-AP groups versus the N group was greater in the ratio of plasma/blood serotonin than in the plasma serotonin level, though the measurements of these variables for the e-AP and u-AP were close to those for the N group.

The results of the p-test (in which values of p<0.05 are considered significant) on the data for the N group and the OMI group, which demonstrated similar means, indicate that there was significant difference in the ratio of plasma/blood serotonin though no significant difference was found in the plasma serotonin level. This suggests that it is preferred to make the diagnosis of the present invention on the basis of the ratio of plasma/blood serotonin than the plasma serotonin level alone in order to accurately know the pathology of vascular endothelial injury (Tables 13 and 14). The results of the p-test on the data for the e-AP and u-AP groups versus the N group also indicate the preference of the ratio of plasma/blood serotonin to the plasma serotonin level (Tables 13 and 14).

Figure 14:
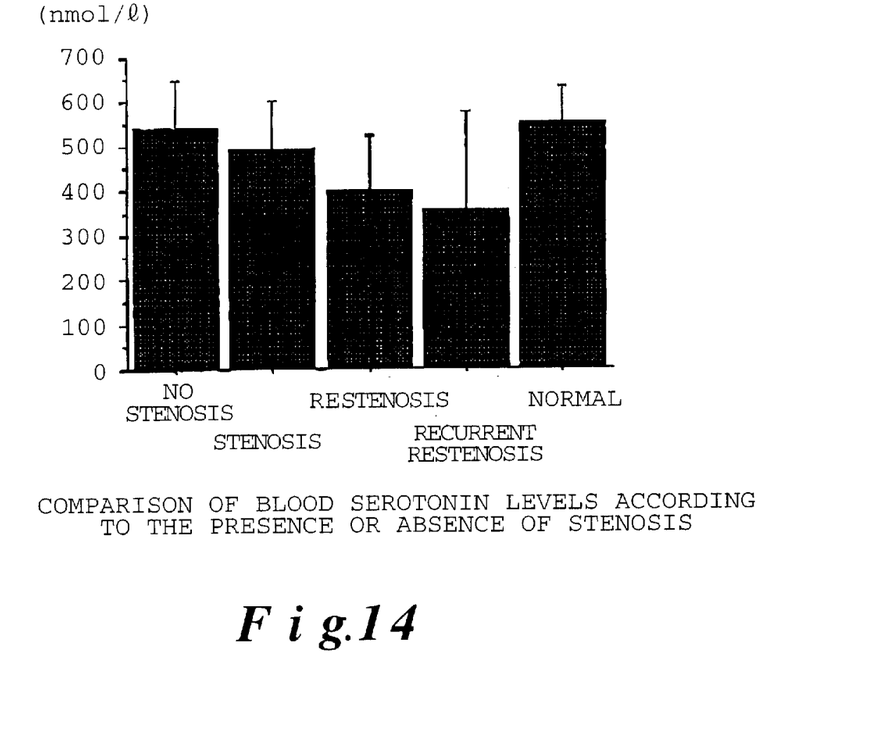
FIG. 14 is a histogram showing the blood serotonin levels determined in Example 4. The error bars in the graph indicate 95% confidence intervals. "No stenosis", "stenosis", "restenosis", "recurrent restenosis" and "normal" denote "a group (A) of patients who were specified as not having at least 50% stenosis by coronary angiography (CAG)", "a group (B) of patients who were specified as having at least 50% stenosis by CAG", "a group (C) of patients who were specified as having at least 70% restenosis by CAG", "a group (D) of patients who were specified as having at least 70% recurrent restenosis by CAG" and a group (N) of normal subjects", respectively.
Figure 15:
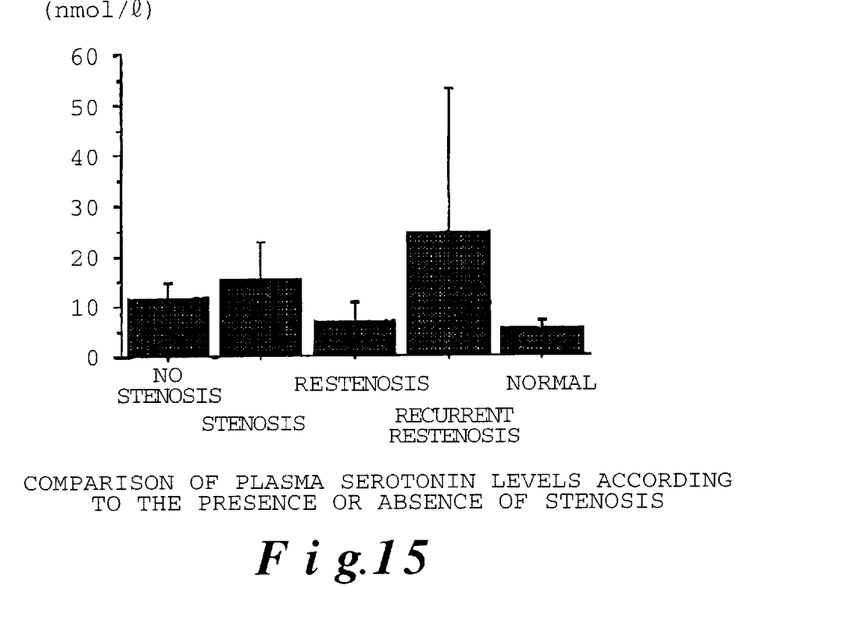
FIG. 15 is a histogram showing the plasma serotonin levels measured in Example 4. The error bars in the graph indicate 95% confidence intervals. "No stenosis", "stenosis", "restenosis", "recurrent restenosis" and "normal" have the same meanings as in FIG. 14.
Figure 16:
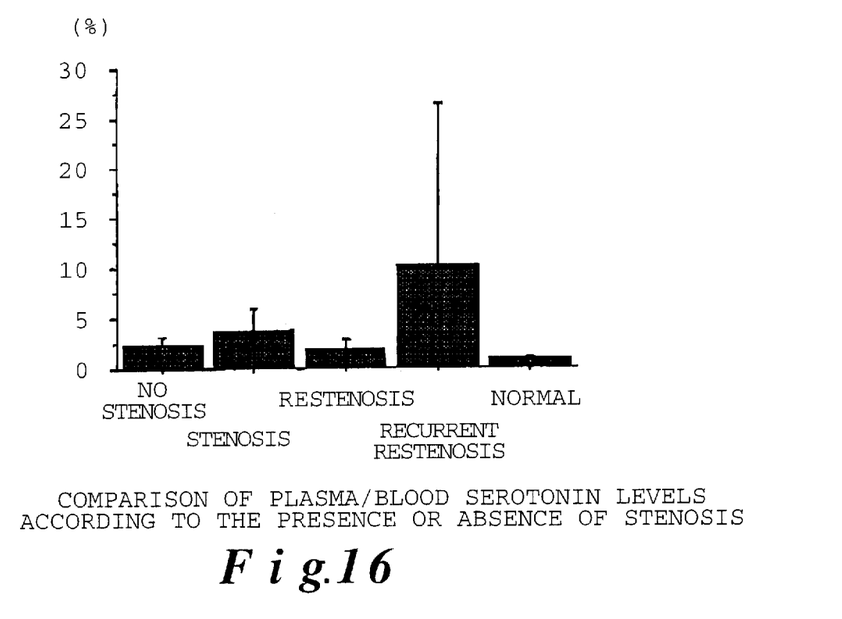
FIG. 16 is a histogram showing the ratios of plasma/blood serotonin measured in Example 4. The error bars in the graph indicate 95% confidence intervals. "No stenosis", "stenosis", "restenosis", "recurrent restenosis" and "normal" have the same meanings as in FIG. 14.

Tables 15 to 17 and FIGS. 14 to 16 show the results of analyses of the data for 62 patients who were clearly diagnosed with or without stenosis by coronary angiography (CAG) among the 65 patients with coronary artery disease who supplied blood sample (the remaining three patients who were not clearly diagnosed with or without stenosis by CAG were excluded) and for the normal subjects (hereinafter referred to as N). The 62 patients were subdivided into a group with at least 50% stenoses (n=46) and a group without stenosis of at least 50% (n=16, 30–79 years old, hereinafter referred to as A), and the former group (n=46) was further classified into a group with at least 70% restenoses (n=13, 50–69 years old, hereinafter referred to as C), a group with at least 70% recurrent restenoses (n=5, 50–79 years old, hereinafter referred to as D) and a group of patients who were specified as having at least 50% stenoses for the first time (n=28, 40–79 years old, hereinafter referred to as B).

The group N demonstrated the highest blood serotonin levels, and the groups A, B, C and D followed in this order. The severity of vascular endothelial injury increase with the number of stenoses, and circulating serotonin is consumed at the sites of vascular endothelial injury through blood coagulation and thrombolysis. The observation that the number of stenoses increases in the order of N, A, B, C and D agrees with the descending order of blood serotonin. The plasma serotonin levels increased in the order of N, A, C, B and D, despite the prediction that the plasma serotonin levels increase in the order of N, A, B, C and D contrary to the ascending order of blood serotonin. This inconsistency suggests that the plasma serotonin level does not always agree with the information on stenosis in the coronary artery because the influence of endothelial injury in capillary arteries is greater than that of endothelial injury in the coronary artery, which is a major artery, though. However, it is sure that the group B (stenosis) has more stenoses than the group A (no stenosis). In fact, the plasma serotonin level and the ratio of plasma/blood serotonin were higher in the group B than in the group A, though there was no significant differences between them.

The p-test (in which values of p<0.05 are considered significant) on the plasma serotonin levels demonstrated significant differences between the groups A, B and D versus the group N, between the group D versus the group A and between the group D versus the group C. There were significant differences in the ratio of plasma/blood serotonin between the groups A, B, C and D versus the group N, between the group D versus the group A and between the group D versus the group C. It is noteworthy that there is a significant difference between the group C versus the group N in the ratio of plasma/blood serotonin but not in the plasma serotonin level.

TABLE 11

Comparison of the measurements for the normal subjects by age

|  | Age of 20–29 | | Age of 40–49 | |
| --- | --- | --- | --- | --- |
|  | Mean | S.D. | Mean | S.D. |
| Blood serotonin (nmol/l) | 619.58 | 173.47 | 515.177 | 166.212 |
| Plasma serotonin (nmol/l) | 7.22 | 4.709 | 5.072 | 4.108 |
| Plasma/blood serotonin (%) | 1.187 | 0.65 | 0.937 | 0.667 |

TABLE 12

The results of the two-tailed Student's t-test on the blood serotonin levels according to pathological conditions

|  | N | OMI | e-AP | u-AP | OMI-1 |
| --- | --- | --- | --- | --- | --- |
| Mean (nmol/l) | 552.24 | 446.76 | 500.09 | 488.35 | 496.38 |
| S.D. (nmol/l) | 172.95 | 263.29 | 235.31 | 151.92 | 262.94 |
| P vs N |  | 0.1425 | 0.4076 | 0.2303 | 0.4321 |
| P vs OMI |  |  | 0.4936 | 0.9699 | 0.5733 |
| P vs e-AP |  |  |  | 0.6425 | 0.9618 |
| P vs u-AP |  |  |  |  | 0.7029 |

TABLE 13

The results of the two-tailed Student's t-test on the plasma serotonin levels according to pathological conditions

|  | N | OMI | e-AP | u-AP | OMI-1 |
| --- | --- | --- | --- | --- | --- |
| Mean (nmol/l) | 5.23 | 7.64 | 9.33 | 12.87 | 23.62 |
| S.D. (nmol/l) | 3.81 | 7.88 | 5.41 | 10.12 | 23.72 |
| P vs N |  | 0.2208 | 0.0059 | 0.0089 | 0.0012 |
| P vs OMI |  |  | 0.4156 | 0.2292 | 0.0104 |
| P vs e-AP |  |  |  | 0.2647 | 0.0066 |
| P vs u-AP |  |  |  |  | 0.3406 |

TABLE 14

The results of the two-tailed Student's t-test on the ratios of plasma/blood serotonin according to pathological conditions

|  | N | OMI | e-AP | u-AP | OMI-1 |
| --- | --- | --- | --- | --- | --- |
| Mean (%) | 0.928 | 1.957 | 2.117 | 3.078 | 6.774 |
| S.D. (%) | 0.514 | 2.245 | 1.407 | 2.406 | 9.192 |
| P vs N |  | 0.0480 | 0.0007 | 0.0006 | 0.0060 |
| P vs OMI |  |  | 0.7787 | 0.3413 | 0.3790 |
| P vs e-AP |  |  |  | 0.2310 | 0.0186 |
| P vs u-AP |  |  |  |  | 0.3904 |

N: normal subjects
OMI: old myocardial infarction (the onset was before more than a year)
e-AP: exertional angina
u-AP: unstable angina
OMI-1: old myocardial infarction (the onset was within a year)

TABLE 15

The results of the two-tailed Student's t-test on the blood serotonin levels according to the presence or absence of stenosis

|  | N | A | B | C | D |
| --- | --- | --- | --- | --- | --- |
| Mean (nmol/l) | 552.24 | 540.32 | 492.18 | 395.77 | 358.25 |
| S.D. (nmol/l) | 172.95 | 202.47 | 282.93 | 206.02 | 174.98 |
| P vs N |  | 0.8482 | 0.3949 | 0.0233 | 0.0339 |
| P vs A |  |  | 0.5534 | 0.0685 | 0.0871 |
| P vs B |  |  |  | 0.279 | 0.3173 |
| P vs C |  |  |  |  | 0.7245 |

TABLE 16

The results of the two-tailed Student's t-test on the plasma serotonin levels according to the presence or absence of stenosis

|  | N | A | B | C | D |
|---|---|---|---|---|---|
| Mean (nmol/l) | 5.23 | 11.41 | 15.28 | 6.85 | 24.76 |
| S.D. (nmol/l) | 3.81 | 6.18 | 19.28 | 6.24 | 22.78 |
| P vs N |  | 0.0006 | 0.0232 | 0.3531 | 0.0006 |
| P vs A |  |  | 0.4423 | 0.0593 | 0.0399 |
| P vs B |  |  |  | 0.1341 | 0.3307 |
| P vs C |  |  |  |  | 0.0158 |

TABLE 17

The results of the two-tailed Student's t-test on the ratios of plasma/blood serotonin according to the presence or absence of stenosis

|  | N | A | B | C | D |
|---|---|---|---|---|---|
| Mean (%) | 0.928 | 2.349 | 3.793 | 1.83 | 10.224 |
| S.D. (%) | 0.514 | 1.544 | 5.546 | 1.66 | 13.006 |
| P vs N |  | 0.0004 | 0.0228 | 0.0259 | 0.0018 |
| P vs A |  |  | 0.3158 | 0.3925 | 0.0213 |
| P vs B |  |  |  | 0.2213 | 0.0668 |
| P vs C |  |  |  |  | 0.0292 |

N: normal subjects
A: no stenosis
B: stenosis
C: restenosis
D: recurrent restenosis

EXAMPLE 5

Fibrinogen, leucocytes, high-sensitivity CRP, total cholesterol, triglyceride, Lp(a) and creatinine kinase in the blood samples collected from the 65 patients with coronary artery disease mentioned in Example 4 were measured to determin if there is correlation with blood serotonin, plasma serotonin and the ratio of plasma/blood serotonin. The results (the squares of the correlation coefficients) are shown in Table 18. Fibrinogen was measured by a thrombin coagulation time method. Leucocytes were counted by flow cytometry with electric resistance detection. High-sensitivity CRP and Lp(a) were measured by latex aggregation nephelometry. Total cholesterol, triglyceride and creatinine kinase were measured enzymatically.

As is evident from Table 18, blood serotonin, plasma serotonin and the ratio of plasma/blood serotonin showed no correlation with the other variables. The lack of correlation indicates that the pathological conditions diagnosed from plasma serotonin are different from those which can be diagnosed from known markers. Thus, the plasma serotonin level is one of the important inspection markers that can not be replaced by any other inspection markers.

TABLE 18

Correlation coefficients ($R^2$) with other inspection markers

|  | Blood serotonin | Plasma serotonin | Plasma/blood serotonin |
|---|---|---|---|
| Fibrinogen | 0.0260 | 0.0393 | 0.0156 |
| Leukocyte count | 0.0754 | 0.0019 | 0.0057 |
| High-sensitivity CRP | 0.0090 | 0.0089 | 0.0043 |
| Total cholesterol | 0.0033 | 0.00004 | 0.0004 |
| Triglyceride | 0.0011 | 0.0054 | 0.0014 |
| Lp (a) | 0.0018 | 0.0004 | 0.0013 |
| Creatinine kinase | 0.0005 | 0.0048 | 0.0209 |

The present invention provides a novel and unfamiliar method for diagnosing vascular endothelial injury or arteriosclerotic pathology. The present invention is characterized by the use of the plasma serotonin level or the ratio of plasma/blood serotonin for diagnosis of vascular endothelial injury or diagnosis of arteriosclerotic pathology.

The present invention can be carried out readily by measuring serotonin by conventional liquid chromatography or immunoassay and preparing plasma samples by a conventional procedure.

The entire disclosure of Japanese Patent Application No. 2000-254236 filed on Aug. 18, 2000 including specification, claims, drawings and summary are incorporated herein by reference in its entirety.

What is claimed is:

1. A method for diagnosing vascular endothelial injury comprising:

a) measuring a serotonin level in a platelet poor plasma sample obtained from a subject, and b) comparing said measured serotonin level to a mean serotonin level measured in platelet poor plasma samples obtained from normal subjects, wherein the serotonin levels are measured by the same method and wherein an elevated serotonin level in said measured serotonin level compared to said mean serotonin level for normal subjects indicates vascular endothelial injury.

2. The method according to claim 1, wherein the vascular endothelial injury arises from coronary artery disease.

3. The method according to claim 1, which is carried out in the presence of from 0.0074 to 0.0148 mole/liter of ethylenediaminetetraacetic acid.

4. A method for diagnosing vascular endothelial injury comprising:

a) measuring a serotonin level in a platelet poor plasma sample obtained from a subject, and b) comparing said measured serotonin level to serotonin levels measured in platelet poor plasma samples obtained at prior times from the same subject, wherein the serotonin levels are measured by the same method, and wherein an elevated serotonin level in said measured serotonin level compared to the serotonin levels in the platelet poor plasma samples obtained at prior times indicates progress of vascular endothelial injury.

5. The method according to claim 4, wherein the vascular endothelial injury arises from coronary artery disease.

6. The method according to claim 4, which is carried out in the presence of from 0.0074 to 0.0148 mole/liter of ethylenediaminetetraacetic acid.

7. A method for diagnosing vascular endothelial injury comprising:

a) measuring a serotonin level in a platelet poor plasma sample obtained from a subject, b) measuring a serotonin level in a whole blood, serum or platelet sample obtained from the same subject at the same time as the platelet poor plasma sample, c) calculating the ratio of the serotonin level measured in a) to the serotonin level measured in b), and d) comparing the ratio calculated in c) to a mean ratio of the serotonin level in platelet poor plasma samples obtained from normal subjects to the serotonin level in whole blood, serum or platelet samples obtained from the same normal subjects, wherein the serotonin levels are measured by the same method, and an elevated ratio obtained from the subject compared to the mean ratio obtained from the normal subjects indicates vascular endothelial injury.

8. The method according to claim 7, wherein the vascular endothelial injury arises from coronary artery disease.

9. The method according to claim 7, which is carried out in the presence of from 0.0074 to 0.0148 mole/liter of ethylenediaminetetraacetic acid.

10. A method for diagnosing vascular endothelia injury comprising:
   a) measuring a serotonin level in a platelet poor plasma sample obtained from a subject,
   b) measuring a serotonin level in a whole blood, serum or platelet sample obtained from the same subject at the same time as the platelet poor plasma sample,
   c) calculating the ratio of the serotonin level measured in a) to the serotonin level measured in b), and
   d) comparing the ratio calculated in c) to the ratios of the serotonin levels in platelet poor plasma samples to the serotonin levels in whole blood, serum or platelet samples obtained at prior times from the same subject,
   wherein serotonin levels are measured by the same method, and wherein an elevated ratio as compared to the ratios obtained at prior times indicates progress of vascular endothelial injury.

11. The method according to claim 10, wherein the vascular endothelial injury arises from coronary artery disease.

12. The method according to claim 10, which is carried out in the presence of from 0.0074 to 0.0148 mole/liter of ethylenediaminetetraaoetic acid.

* * * * *